| United States Patent [19] | [11] Patent Number: 5,210,351 |
|---|---|
| Venier et al. | [45] Date of Patent: *May 11, 1993 |

[54] PREPARATION OF ALKYLATED CYCLOPENTADIENES

[75] Inventors: Clifford G. Venier; Edward W. Casserly, both of The Woodlands, Tex.

[73] Assignee: Pennzoil Products Company, Houston, Tex.

[ * ] Notice: The portion of the term of this patent subsequent to Jan. 26, 2005 has been disclaimed.

[21] Appl. No.: 754,467

[22] Filed: Sep. 4, 1991

Related U.S. Application Data

[60] Continuation-in-part of Ser. No. 660,469, Feb. 25, 1991, Pat. No. 5,144,095, which is a continuation-in-part of Ser. No. 323,749, Mar. 15, 1989, Pat. No. 5,012,022, which is a continuation of Ser. No. 170,654, Mar. 15, 1988, abandoned, which is a division of Ser. No. 112,378, Oct. 22, 1987, Pat. No. 4,849,566, and a continuation-in-part of Ser. No. 323,164, Mar. 15, 1989, Pat. No. 4,929,782, which is a continuation of Ser. No. 170,653, Mar. 15, 1988, abandoned, which is a division of Ser. No. 112,378, Mar. 15, 1988, and a continuation-in-part of Ser. No. 323,906, Mar. 15, 1989, Pat. No. 5,012,023, which is a continuation-in-part of Ser. No. 170,652, Mar. 15, 1988, abandoned, which is a division of Ser. No. 112,378, Mar. 15, 1988, said Ser. No. 112,378, is a continuation-in-part of Ser. No. 909,305, Sep. 19, 1986, Pat. No. 4,721,823.

[51] Int. Cl.$^5$ ............................................. C07C 2/86
[52] U.S. Cl. ..................................... 585/375; 585/467
[58] Field of Search ................ 585/318, 327, 375, 467

[56] References Cited

U.S. PATENT DOCUMENTS 4,721,823  1/1988  Venier et al. ...................... 585/375
4,929,782  5/1990  Venier et al. ...................... 585/375
5,068,469  11/1991  Young et al. ..................... 568/868

Primary Examiner—Asok Pal
Assistant Examiner—P. Achutamurthy
Attorney, Agent, or Firm—Lowe, Price, LeBlanc & Becker

[57] ABSTRACT

Cyclopentadienes are alkylated by initially reacting primary or secondary alcohols at elevated temperatures in the presence of an alkali metal hydroxide with removal of water to form dimers of said primary or secondary alcohols, and thereafter reacting said alcohol dimers with a cyclopentadiene to alkylate said cyclopentadiene.

7 Claims, No Drawings

PREPARATION OF ALKYLATED CYCLOPENTADIENES

CROSS REFERENCE TO RELATED APPLICATIONS

This is a continuation-in-part of application Ser. No. 660,469, filed Feb. 25, 1991, now U.S. Pat. No. 5,144,095, which is a continuation-in-part of application Ser. No. 323,749 filed Mar. 15, 1989, now U.S. Pat. No. 5,012,022 which is a continuation of application Ser. No. 170,654, filed Mar. 15, 1988, now abandoned, which is a division of application Ser. No. 112,378, filed Oct. 22, 1987, now U.S. Pat. No. 4,849,566; and is a continuation-in-part of application Ser. No. 323,164, filed Mar. 15, 1989, now U.S. Pat. No. 4,929,782, which is a continuation of application Ser. No. 170,653, filed Mar. 15, 1988, now abandoned, which is a division of said application Ser. No. 112,378; and is a continuation-in-part of application Ser. No. 323,906, filed Mar. 15, 1989, now U.S. Pat. No. 5,012,023, which is a continuation-in-part of application Ser. No. 170,652, filed Mar. 15, 1988, now abandoned, which is a division of said application Ser. No. 112,378, said application Ser. No. 112,378 being a continuation-in-part of application Ser. No. 909,305, filed Sep. 19, 1986, now U.S. Pat. No. 4,721,823.

FIELD OF INVENTION

This invention relates to alkylated cyclopentadienes, their use as lubricating compositions and methods of manufacture. More particularly, this invention relates to a novel method for preparation of alkylated cyclopentadienes.

BACKGROUND

Cyclopentadienes and alkylated derivatives thereof are known in the art. Further, methods are known for preparation of alkylated cyclopentadienes. There is described in Applicant's prior filed applications which have issued as U.S. patents, novel cyclopentadienes, their use as synthetic lubricant compositions and methods for their preparation. The cyclopentadienes invented previously by Applicant's are disclosed in prior U.S. Pat. Nos. 4,849,566, 4,929,782, and 4,721,823. The disclosures of these prior filed U.S. patents are specifically incorporated herein by reference as these patents described the classes of alkylated cyclopentadienes which can be prepared according to the present invention using cyclopentadiene starting materials.

SUMMARY OF INVENTION

It is accordingly an object of the present invention to provide a process for the preparation of alkylated cyclopentadienes.

A further object of the invention is to provide a method for the preparation of alkylated cyclopentadienes from primary and secondary alcohols at elevated temperatures.

Other objects and advantages of the invention will become apparent as the description thereof proceeds.

In satisfaction of the foregoing objects and advantages, there are provided by the present invention a method for the preparation of alkylated cyclopentadienes comprising the reaction of primary or secondary alcohols at elevated temperatures in the presence of a base with removal of water to produce an alcohol dimer which has a formula equal to the sum of the two reacting alcohol molecules less the water molecules which are being removed. In a second step, this dimer alcohol is reacted with a cyclopentadiene to produce alkylated cyclopentadiene.

DETAILED DESCRIPTION FOR THE INVENTION

The present invention is broadly concerned with the preparation of novel alcohol cyclopentadienes which are useful as synthetic lubricants in lubricating compositions, or in combination with a lubricant additive. The invention is specifically concerned with preparation of a class of alkyl substituted cyclopentadienes which may be described by the following general formula:

wherein, in the above formula, each $R_1$ is selected from the group consisting of hydrogen and alkyl groups of 1 to 6 atoms, and each $R_2$ is individually and independently selected from the group consisting of individual and independent hydrocarbyl groups, preferably straight or branched chained alkyl groups of 4 to 36 carbon atoms, preferably 8 to 36 carbon atoms, more preferably 12 to 24 carbon atoms, z is 0, 1, 2, or 3 and y is 2, 3, 4, 5, or 6.

According to the present invention, there has been discovered a new process for the preparation of alkylated cyclopentadienes by a reaction involving an initial step wherein primary or secondary alcohols are reacted in the presence of a base, preferably an alkali metal hydroxide, at an elevated temperature in the range of above 200° C. to produce an alcohol dimer which has a formula equal to the sum of the two reacting molecules, less a molecule of water. During the reaction, water is produced and is removed in order to permit the reaction to proceed.

This reaction is generally known as the Guerbet reaction, a known reaction to produce alcohol dimers by this method.

Once the initial reaction is complete, the resulting alcohol is then used without purification to alkylate cyclopentadienes. In the alkylation reaction, the cyclopentadiene starting material is reacted with the dimer alcohol obtained from the first step in combination with a basic catalyst such as an alkali metal hydroxide in a reaction vessel. The alcohol reactant is used in sufficient amounts to provide a molar excess of about 3 to 6 moles.

In practice, the alcohols contained in the reaction vessel are brought to temperature. The cyclopentadiene or substituted cyclopentadiene is then added to the reaction vessel at room temperature or at a temperature as high as the reflux temperature of the mixture, which would be about the boiling temperature of the alcohol reactant. Alternatively, a portion of the cyclopentadiene may be mixed with the alcohol and basic catalyst in the reactor and the remaining cyclopentadiene starting material added to the reaction mixture over a period of time as the reaction proceeds.

An inert solvent may also be included if necessary, depending on the alcohol reactants. The reaction may be carried out in a closed container so that higher temperatures in excess of 180° and up to 260° C. can be reached. As the reaction proceeds, water will be produced and is removed as it is formed. This is an important feature of the invention, since it appears to drive the reaction to completion and increase yields substantially.

On completion of the reaction, the mixture is allowed to cool and then mixed with water or poured on ice and two layers allowed to separate. The organic and aqueous layers are separated using an organic solvent to aid the separation if necessary. After removal of excess alcohol and any solvent from the organic layer, the alkylated cyclopentadiene is recovered.

In an alternative workup procedure, the reaction mixture may be filtered and the alcohol separated by distillation before or after filtration.

In conducting this alkylation reaction, minor side products may be formed. For example, the acid corresponding to the alcohol and a dimeric alcohol may also be formed. The careful exclusion of oxygen and careful adjustment of the alcohol base ratios aid in suppression of the formation of these products. If secondary alcohols are used, the by-products are less significant.

The alcohol alkylation is preferably carried out in the range of 180°-300° C. for a reaction time which may range from 10 minutes to 3 days. The mole ratio of alcohol to cyclopentadiene may range from 1:1 up to 5:1 and the ratio of alkali metal hydroxide to cyclopentadiene reacted may range from 0.1:1 up to 10:1.

It is a feature of the invention that the alcohol preparation step and the alkylation step may be carried out in a single reaction vessel to combine the steps in a synergistic manner. Thus the alcohol dimer is formed by reaction of the alcohol starting material and alkali metal hydroxide at the temperature range of 200°-250° C. with removal of water. At this stage, while maintaining the same reactor and maintaining the prepared alcohol at temperature and with the same catalyst, the second stage can be carried out by simply adding the cyclopentadiene starting material to the reactor to initiate the alkylation reaction. The reaction is then completed and product recovered as described above.

The following examples are presented to illustrate the invention, but the invention is not to be considered as limited thereto. In the examples, and throughout the specification, parts are by weight unless otherwise indicated.

EXAMPLE

N-Decyl alcohol (6 mol) is reacted with potassium hydroxide (3 mol) in aqueous solution at a temperature of 225° C. while removing water from the reaction as it occurs. On the completion of removal of water, there is formed in the reaction flask, a $C_{20}$ alcohol. While still maintaining the reaction temperature, there is then added to the reaction flask containing the prepared alcohol, cyclopentadiene (1 mol) over a period of 1 hour. As the reaction proceeds, the water produced from the reaction is removed as it is formed.

On completion of the reaction, the mixture is allowed to cool and then poured onto ice from which two layers are allowed to separate. The organic and aqueous layers are separated and the $C_{20}$ alkylated cyclopentadiene recovered.

The invention has been described with references said preferred embodiments. However, as obvious variations thereon will become apparent to those skilled in the art, the invention is not to be considered as limited thereto.

We claim:

1. In a process for the preparation of alkylated cyclopentadienes by reacting a dimer of a primary or secondary alcohol with a cyclopentadiene to alkylate the cyclopentadiene and form an alkylated cyclopentadiene product comprising forming said dimer by reacting a primary or secondary alcohol in the presence of an alkali metal hydroxide catalyst at a temperature range of $200°-250\frac{1}{2}°$ C. with removal of water to produce said dimer of said primary or secondary alcohol, and reacting said dimer of said primary or secondary alcohol with said cyclopentadiene to alkylate said cyclopentadiene; the improvement comprising:

reacting said dimer of said primary or secondary alcohol with said cyclopentadiene only after the reaction of said primary or secondary alcohol and the removal of said water is complete.

2. A process according to claim 1, wherein the primary or secondary alcohol contains from 4 to 36 carbon atoms.

3. A process according to claim 2, wherein the cyclopentadiene starting material is cyclopentadiene or alkyl-substituted cyclopentadiene.

4. A process according to claim 1, wherein the alkali metal hydroxide is potassium hydroxide.

5. A process according to claim 1, wherein the cyclopentadiene reactant is added to said alcohol dimer without isolation of said dimer.

6. A process according to claim 1, wherein the alcohol preparation step and the alkylation step is carried out in a single reaction vessel without purification of the dimer alcohol.

7. A process according to claim 6, wherein the cyclopentadiene starting material is added while maintaining said reaction vessel at said temperature range of 200°-250° C.

* * * * *